United States Patent [19]

Schubert et al.

[11] Patent Number: 5,482,953
[45] Date of Patent: Jan. 9, 1996

[54] 2,4-AND 2,5-BISTETRAZOLYLPYRIDINES AND THE USE THEREOF AS PHARMACEUTICALS

[75] Inventors: Gerrit Schubert, Kelkheim; Ekkehard Baader, Königstein; Martin Bickel, Bad Homburg; Volkmar Günzler-Pukall, Marburg, all of Germany

[73] Assignee: Hoechst Aktiengesellschaft, Frankfurt am Main, Germany

[21] Appl. No.: 183,786

[22] Filed: Jan. 21, 1994

Related U.S. Application Data

[63] Continuation of Ser. No. 829,295, Feb. 3, 1992, abandoned.

[30] Foreign Application Priority Data

Feb. 5, 1991 [DE] Germany .......................... 41 03 372.8

[51] Int. Cl.[6] .................................................. A61K 31/44
[52] U.S. Cl. ............................................ 514/340; 546/276
[58] Field of Search ............................................. 514/340

[56] References Cited

U.S. PATENT DOCUMENTS

| 4,717,727 | 1/1988 | Gunzler et al. | 514/354 |
|---|---|---|---|
| 4,968,670 | 11/1990 | Brocks et al. | 514/354 |
| 5,013,736 | 5/1991 | Nagahara et al. | 514/255 |
| 5,037,839 | 8/1991 | Bickel et al. | 514/354 |

FOREIGN PATENT DOCUMENTS

| 11450/88 | 8/1988 | Australia . |
|---|---|---|
| 39263/89 | 2/1990 | Australia . |
| 59144/90 | 1/1991 | Australia . |
| 69366/91 | 7/1991 | Australia . |
| 79356/91 | 1/1992 | Australia . |

OTHER PUBLICATIONS

Wade . Organic Chemistry . Prentice–Hall. New Jersey 1987. p. 349.
Suarez et al. Heterocyclic Chem. 15. 1093–1096 1978.
Zeffren et al. The Study of Enzyme Mechanism p. 87. 1974.
Haring, M., et al., Helvetica Chemica Acta, 37(17):147–153 (1954).
Itai, T., et al., Bulletin National Institute of Hygiene, 74:115–117 (1956).
Shinohara, et al., Chemistry High Polymers, Japan, 15:839–849 (1958).
Hirakata, T. et al., J. Pharm. Soc. Japan, 77:219–221 (1957).
Majamaa, K. et al., Eur. J. Biochem, 138:239–245 (1984).
Tschank, G. et al., Biochem. J., 248:625–633 (1987).

*Primary Examiner*—Jane Fan
*Attorney, Agent, or Firm*—Finnegan, Henderson, Farabow, Garrett & Dunner

[57] ABSTRACT

The invention relates to 2,4- and 2,5-bistetrazolylpyridines. Said compounds inhibit the enzymes proline hydroxylase and lysine hydroxylase and bring about a selective inhibition of collagen biosynthesis. They are used as fibrosuppressants and immunosuppressants.

1 Claim, No Drawings

2,4-AND 2,5-BISTETRAZOLYLPYRIDINES AND THE USE THEREOF AS PHARMACEUTICALS

This application is a continuation of application Ser. No. 07/829,295, filed Feb. 3, 1992, now abandoned.

Compounds which inhibit the enzymes proline hydroxylase and lysine hydroxylase bring about very selective inhibition of collagen biosynthesis by influencing the collagen-specific hydroxylation reaction. In the course of this, protein-bound proline or lysine is hydroxylated by the enzymes proline hydroxylase or lysine hydroxylase respectively. If this reaction is suppressed by inhibitors, the resulting collagen molecule is underhydroxylated, is unable to function and can be released by the cells into the extracellular space only in small amount. The underhydroxylated collagen is additionally unable to be incorporated in the collagen matrix and very easily undergoes proteolytic degradation. The consequence of these effects is an overall reduction in the amount of collagen deposited outside the cells.

It is known that the inhibition of proline hydroxylase by known inhibitors such as α,α-dipyridyl leads to inhibition of $Cl_q$ biosynthesis by macrophages (W. Müller et al., FEBS Lett. 90 (1978), 218; Immunobiology 155 (1978), 47). This results in the classical pathway of complement activation becoming inoperative. Inhibitors of proline hydroxylase therefore also act as immunosuppressants, for example in immune complex diseases.

It is known that the enzyme proline hydroxylase is efficiently inhibited by pyridine-2,4- and -2,5-dicarboxylic acid (K. Majamaa et al., Eur. J. Biochem. 138 (1984)239–245). These compounds are, however, active as inhibitors in cell culture only in very high concentration (Tschank, G. et al., Biochem. J. 248 (1987) 625–633).

DE-A 34 32 094 describes pyridine-2,4- and -2,5-dicarboxylic diesters with 16 carbon atoms in the ester alkyl moiety as pharmaceuticals for inhibiting proline hydroxylase and lysine hydroxylase.

However, these lower alkyl diesters have the disadvantage that they are too quickly cleaved to the acids in the body and do not reach their site of action in the cell in sufficiently high concentration and thus are less suitable for possible administration as pharmaceuticals.

DE-A 37 03 959, DE-A 37 03 962 and DE-A 37 03 963 describe, in general form, mixed esters/amides, higher alkylated diesters and diamides of pyridine-2,4- and -2,5-dicarboxylic acid, which effectively inhibit collagen biosynthesis in an animal model. Thus, DE-A 37 03 959 describes, inter alia, the synthesis of N,N'-bis(2-methoxyethyl)pyridine-2,4-dicarboxamide and N,N'-bis(3-isopropoxypropyl)pyridine-2,4-dicarboxamide.

German Patent Applications P 38 26 471.4 and P38 28 140.6 propose an improved process for the preparation of N,N'-bis(2-methoxyethyl)pyridine-2,4-dicarboxamides.

German Patent Application P 39 24 093.2 proposes novel N,N'-bis(alkoxyalkyl)pyridine-2,4-dicarboxamides.

German Patent Application P 40 01 002.3 describes the use of di(nitroxyalkyl) amides of pyridine-2,4- and -2,5-dicarboxylic acids for the preparation of pharmaceuticals inhibiting proline hydroxylase and lysine hydroxylase.

Both pyridine-2,4 - and -2,5-dicarboxamide (Hirakata et al., J. Pharm. Soc. Japan 77 (1957) 219 and Häring et al., Helv. 37 (1954) 147, 153), and pyridine-2,4- and -2,5-dicarbohydrazide (Itai et al., Bl. Nation. Hyg. Labor. Tokyo, 74 (1956) 115, 117 and Shinohara et al., Chem. High Polymers, Japan, 15 (1958) 839) have already been disclosed as agents for tuberculosis.

JP 53/28175 (78/28175) describes N,N'-bis(2-nitroxyethyl)pyridine-2,4 -2,4- and -2,5-dicarboxamides as substances with a vasodilator effect.

German Patent Application P 40 20 570.3 describes the use of 2,4- and 2,5-substituted pyridine N-oxides for the preparation of pharmaceuticals inhibiting proline hydroxylase and lysine hydroxylase.

It has now been found, surprisingly, that 2,4 - and 2,5-bistetrazolylpyridines of the formula I indicated below, and the physiologically tolerated salts thereof, effectively inhibit lysine hydroxylase and proline hydroxylase in an animal model.

Specific 2,4- and 2,5-bistetrazolylpyridines are compounds of the formula I

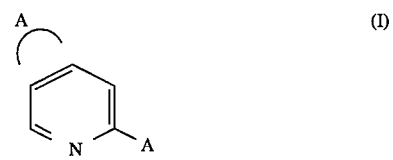

where A is

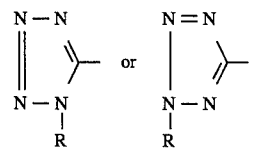

and where R is H, $(C_2-C_6)$alkyl, $(C_2-C_6)$alkenyl, $(C_2-C_6)$alkynyl, but preferably in each case alkyl where appropriate, substituted by carboxyl or carboxy$(C_1-C_4)$alkyl ester, by arylcarbonyl, especially phenylcarbonyl, by $(C_1-C_4)$alkylaminocarbonyl, where substitution by $(C_1-C_6)$alkoxy, especially $(C_1-C_4)$alkoxy, is possible for alkyl in turn, by aminocarbonyl, where the nitrogen can be substituted once, but preferably twice, by alkyl, especially $(C_1-C_3)$alkyl, $(C_6-C_{10})$aryl, especially phenyl or naphthyl, where appropriate substituted by halogen (chlorine or bromine), $(C_1-C_6)$alkyl or $(C_1-C_3)$alkoxy, Ar$(C_2-C_6)$alkyl, where one or more, but a maximum of 3, $CH_2$ groups in the alkyl radical can, where appropriate, be replaced by hetero atoms, especially N, O or S, and Ar is, in particular, phenyl, cycloalkyl- or cycloalkenyl-$(C_0-C_6)$alkyl, especially $(C_5-C_6)$cycloalkyl or -alkenyl, where appropriate with aryl ring, especially benzene ring, fused on, where 1 to 3 $CH_2$ groups in the cycle are replaced by hereto atoms such as O, S or N, especially O and/or N, and/or groups such as C=O, and the cycle can, where appropriate, also be substituted by alkyl, especially $(C_1-C_4)$alkyl.

Particularly preferred are alkyl radicals with 1–4 carbon atoms, Ar$(C_1-C_4)$alkyl with one $CH_2$ group in the alkyl radical replaced by a hetero atom, especially N or O, cycloalkyl or cycloalkenyl, where, if two $CH_2$ a groups have each been replaced by a C=O group, a third $CH_2$ group is replaced by N, or, if two $CH_2$ groups have each been replaced by one O, a third group is replaced by C=O or N. The resulting compounds are, in particular, axially symmetrical, i.e. the third group in each case is bonded to the other two.

Particularly preferred compounds of the formula I are those in which the radicals R are identical for both substituents A. To be understood as preferred among these are those compounds for which the substitution patterns for A (2,4 or 2,5 ) are identical.

The invention also relates to a process for the preparation of compounds of the formula I, in which a compound of the formula II

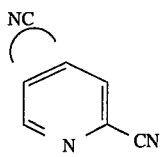

is reacted with NaN$_3$ and NH$_4$Cl in a suitable organic solvent.

If the intention is to obtain compounds of the formula I in which R is not H, the said reaction is then followed by a substitution reaction in which R is replaced by the particular substituent. For this, a solution of 2,4- or 2,5-bis(5-tetrazolyl)pyridine in a suitable solvent, preferably DMF or acetone, is mixed at room temperature with an excess of a suitable base, for example triethylamine or NaOH. Subsequently, for example, an alkylating agent is added as such or dissolved in DMF, and the reaction mixture is left to stir or is heated to boiling under reflux until little or no precursor is still detectable by thin-layer chromatography (silica gel, mobile phase ethyl acetate). Excess alkylating agent is, where appropriate, decomposed by addition of concentrated ammonia. Working up is carried out by either a) evaporation of the mixture and purification by flash chromatography or recrystallization of the residue or b) partition between water and a suitable solvent, preferably ethyl acetate or CH$_2$Cl$_2$, drying of the organic phases with Na$_2$SO$_4$, evaporation of the solution and purification by flash chromatography or recrystallization of the residue.

The compounds of the formula I according to the invention have valuable pharmacological properties and display, in particular, activity as inhibitors of proline hydroxylase and lysine hydroxylase, as fibrosuppressant and as immunosuppressant.

Fibrogenase activity can be determined by radioimmunological determination of the N-terminal propeptide of collagen type III or of the N- or C-terminal crosslinking domain of collagen type IV (7s collagen or type IV collagen NC$_1$) in serum.

For this purpose, the hydroxyproline, procollagen III peptide, 7s collagen and type IV collagen NC$_1$ concentrations were measured in the livers of a) untreated rats (control)

b) rats to which tetrachloromethane had been administered (CCl$_4$ control)

c) rats to which initially CCL$_4$ and then a compound according to the invention had been administered (this test method is described by Roullier, C., experimental toxic injury of the liver; in The Liver C. Roullier, Vol. 2, pages 335–476, New York, Academic Press, 1964).

The compounds of the formula I can be used as medicaments in the form of pharmaceutical products which contain them, where appropriate together with tolerated pharmaceutical vehicles. The compounds can be used as medicines, for example in the form of pharmaceutical products which contain these compounds mixed with an inorganic or organic pharmaceutical vehicle suitable for enteral, percutaneous or parenteral administration, such as, for example, water, gum arabic, gelatin, lactose, starch, magnesium stearate, talc, vegetable oils, polyalkylene glycols, vaseline etc.

They can be administered for this purpose orally in doses of 0.01–25.0 mg/kg/day, preferably 0.01–5.0 mg/kg/day, or parenterally in doses of 0.001–5 mg/kg/day, preferably 0.001–2.5 mg/kg/day, especially 0.005–1.0 mg/kg/day. The dosage can also be increased in severe cases. However, lower doses often suffice in many cases. These data are based on an adult weighing about 75 kg.

The invention also embraces the use of the compounds according to the invention for the preparation of pharmaceuticals which are employed for the treatment and prophylaxis of the abovementioned metabolic disorders.

The invention additionally relates to pharmaceuticals which contain one or more compounds of the formula I according to the invention and/or the physiologically tolerated salts thereof.

The pharmaceuticals are prepared by processes which are known per se and are familiar to the person skilled in the art. As pharmaceuticals, the pharmacologically active compounds (=active substance) according to the invention are employed either as such or, preferably, in combination with suitable pharmaceutical auxiliaries or excipients in the form of tablets, coated tablets, capsules, suppositories, emulsions, suspensions or solutions, where the active substance content is up to about 95%, advantageously between 10 and 75%.

Examples of suitable auxiliaries and excipients for the required pharmaceutical formulation are, besides solvents, gel formers, suppository bases, tablet auxiliaries and other active substance vehicles, also antioxidants, dispersants, emulsifiers, antifoam agents, flavorings, preservatives, solubilizers or colorants.

The active substances can be administered orally, parenterally or rectally.

The active compounds are mixed with the additives suitable for this purpose, such as excipients, stabilizers or inert diluents, and converted by conventional methods into suitable dosage forms such as tablets, coated tablets, hard gelatin capsules, aqueous, alcoholic or oily suspensions or aqueous or oily solutions.

Examples of inert excipients which can be used are gum arabic, magnesia, magnesium carbonate, potassium phosphate, lactose, glucose or starch, especially corn starch. Preparation can take place both as wet and as dry granules. Examples of suitable oily excipients or solvents are vegetable or animal oils, such as sunflower oil or fish liver oil.

For subcutaneous or intravenous administration, the active compounds are converted into solution, suspension or emulsion, if required with substances suitable for this purpose, such as solubilizers, emulsifiers or other auxiliaries. Examples of suitable solvents are physiological saline or alcohols, for example ethanol, propanol, glycerol, as well as sugar solutions such as glucose or mannitol solutions, or else a mixture of the various solvents mentioned.

The invention is explained in more detail by means of examples hereinafter.

2,4-bis (5-Tetrazolyl) pyridine (1)

A mixture of 100 g of 2,5-dicyanopyridine, 122.8 g of NaN$_3$ and 12.8 g of NH$_4$Cl in 910 ml of abs. DMF was heated at 80°–100° C. for 36 h. The paste of beige crystals which formed was mixed with 500 ml of H$_2$O and then acidified to pH 1 with conc. HCl while stirring and cooling in ice. The paste which formed was filtered off with suction, and the residue was dissolved in about 1 l of 2N NaOH solution while stirring and filtered. Renewed acidification to pH 1 with conc. HCl was followed by filtration with suction again, and the residue was dried in vacuo at 50° C. 165.0 g (99%) of 1, beige crystals, melting point 265°–267° C. (decomposition) were obtained.

$^1$H NMR (60 MHz, DMSO-d$_6$) δ=8.1 (dd, J=6 Hz, J'=2 Hz, 1H), 8.8 (s, 1H), 9.0 (d, J=5 Hz, 1H), 7–10 (bs, 2H) ppm. C$_7$H$_6$N$_9$ calc. 216 found 216 (M$^+$+H$^+$).

2,5-bis(5-Tetrazolyl)pyridine (2)

230 mg of 2,5-dicyanopyridine, 283 mg of $NaN_3$ and 36 mg of $NH_4Cl$ were suspended in 3 ml of abs. DMF and stirred at 80°–100° C. for 36 h. After cooling, the mixture was diluted with $H_2O$, filtered through Amberlite IR-120 ($H^+$ form) and washed with $H_2O$. The filtrate was evaporated in vacuo: 348 mg (91%) of 2, colorless crystals, melting point >200° C.

$^1H$ NMR (60 MHz, DMSO-$d_6$) δ=5.5–8.0 (bs), 8.6 (m, 2H), 9.5 (s, 1H) ppm. $C_7H_6N_9$ calc. 216 found 216 ($M^+$+$H^+$).

Isomeric 2,4-bis(methyl-5-tetrazolyl)pyridines (3a, b)

0.69 ml (11.2 mmol) of methyl iodide was added by syringe to a suspension of 1.2 g of 2,4-bis(5-tetrazolyl)pyridine in 15 ml of acetone at room temperature. Subsequently, sufficient 2N NaOH solution was added to produce a clear solution (about 6 ml), and the solution was heated to boiling under reflux while stirring. After 2 h, a further 0.69 ml of methyl iodide was added dropwise. After a total reaction the of 5 h, the mixture was cooled and 10 ml of conc. ammonia solution were added. The mixture was extracted several times with $CH_2Cl_2$, and the organic phases were dried and evaporated in vacuo. 2.21 g of an oil were obtained and were purified on a silica gel column (200 g) with ethyl acetate as eluent. 0.74 g of 3a, colorless crystals of melting point 198°–198.5° C. (ethyl acetate/cyclohexane), $^1H$ NMR (60 MHz, $CDCl_3$) δ=4.5 (s, 3H), 4.6 (s, 3H), 8.2 (dd, J=5 Hz, J'=2 Hz, 1H), 8.9 d (J=5 Hz, 1H), 9.1 (s, 1H) ppm. $C_9H_{10}N_9$ calc. 244 found 244 ($M^+$+$H^+$)

and 0.29 g of 3b, colorless crystals of melting point 214°–215° C. (ethyl acetate/cyclohexane), $^1H$ NMR (60 MHz, $CDCl_3$) δ=4.5 (s, 6H), 8.2 (dd, J=5 Hz, J'=2 Hz, 1H), 8.95 d (J=4 Hz, 1H) overlapped by: 9.0 (s, 1H) ppm. $C_9H_{10}N_9$ calc. 244 found 244 ($M^+$+$H^+$)

2,5-bis(2-Methyl-5-tetrazolyl)pyridine (4)

0.85 ml of $CH_3I$ was added by syringe to a solution of 1.5 g of 2,4-bis(5-tetrazolyl)pyridine and 1.4 ml of triethylamine in 7 ml of abs. DMF, and the mixture was heated to boiling under reflux while stirring for 8 h. After cooling, 10 ml of conc. ammonia solution were added. The mixture was extracted several times with ethyl acetate, and the organic phases were dried and evaporated in vacuo. The residual oil was purified on a silica gel column (200 g) with heptane/ethyl acetate 1:1 as eluent. Colorless needles, melting point 225°–226° C.

$^1H$ NMR (DMSO-$d_6$, 60 MHz) δ=4.5 (s, 3H), 4.55 (s, 3H), 8.6 (m, 2H), 9.5 (s, 1H) ppm. $C_9H_{10}N_9$ calc. 244 found 244 ($M^+$+$H^+$)

Isomeric 2,4-bis(phenacyl-5-tetrazolyl)pyridines (5a, b)

1.4 ml of $NEt_3$ were added dropwise by syringe to a suspension of 1.5 g of 2,4-bis(5-tetrazolyl)pyridine in 7 ml of abs. DMF. The resulting clear solution was stirred at room temperature while 2.78 g of phenacyl bromide were added all at once. The solution became cloudy after a few minutes. After 2 h, ethanol was added and, after filtration, the filtrate was evaporated in vacuo. The residual yellow oil was chromatographed on a silica gel column (200 g) with ethyl acetate/heptane 2:1 as eluent: 541 mg of 5a, colorless fine needles, melting point: 164°–165° C. (ethyl acetate), 1H NMR (60 MHz, $CDCl_3$) δ=6.2 (s, 1H), 6.5 (s, 2H), 7.7 (m, 6H), 8.0–8.3 (sh, 5H), 8.6 (d, J=6 Hz, 1H), 9.2 (s, 1H) ppm. $C_{23}H_{18}N_9O_2$ calc. 452 found 452 ($M^+$+$H^+$)

611 mg of 5b, colorless crystalline powder, melting point 188°–189° C. (decomposition).

$^1H$ NMR (60 MHz, $CDCl_3$) δ=6.3 (s, 6H), 7.5 (m, 6H), 7.9–8.3 (sh, 3H), 8.8–9.2 (m, 2H) ppm. $C_{23}H_{18}N_9O_2$ calc. 452 found 452 ($M^+$+$H^+$)

2,4-bis[2-(N-2-Methoxyethylacetamido)-5-tetrazolyl]pyridine (6)

2-Methoxyethylamide of chloroacetic acid 39.7 ml of chloroacetyl chloride were added dropwise to a vigorously stirred mixture, cooled to −10° to −15° C., of 30.09 g of 2-methoxyethylamine, 100 g of 20 percent strength aqueous NaOH solution and 150 ml of 1,2-dichloroethane. After 1 h, the phases were separated and the aqueous phase was extracted twice with $CH_2Cl_2$. The combined organic phases were washed successively with 2N HCl, saturated $NaHCO_3$ solution and $H_2O$, and the organic phases were dried. The residue after evaporation of the solvent was 60.3 g of a colorless oil which was used further without further purification.

A solution of 1.5 g of 2,4-bis(5-tetrazolyl)pyridine, 1.4 ml of triethylamine and 2.12 g of 2-methoxyethylamide of chloroacetic acid in 7 ml of DMF was heated, with the addition of a spatula tip of KI, at 80° C. for 48 h. The mixture was then cooled, diluted with ethyl acetate and filtered. On concentration of the filtrate, 1.46 g of 6 crystallized, colorless crystals, melting point 192°–194° C.

$^1H$ NMR (60 MHz, DMSO-$d_6$) δ=3.3 (sh, 14H), 5.6 (bs, 4H), 8.1–9.1 (sh, 5H) ppm. $C_{17}H_{24}N_{11}O_4$ calc. 446 found 446 ($M^+$+$H^+$)

2,5-bis[2-(N-2-Methoxyethylacetamido)-5-tetrazolyl]pyridine (7)

was prepared in analogy to 2,4-bis[2-(N-2-methoxyethylacetamido)5-tetrazolyl]pyridine. Colorless crystalline powder, melting point 250° C. (decomposition).

$^1H$ NMR (DMSO-$d_6$, 60 MHz) δ=3.1–3.5 (sh, 14H), 5.65 (s, 4H), 8.3–9.0 (sh, 4H), 9.45 (m, 1H) ppm. $C_{17}H_{24}N_{11}O_4$ calc. 446 found 446 ($M^+$+$H^+$)

2,4-bis [2-(Phthalimidomethyl)-5-tetrazolyl]pyridine (8)

A solution of 1 g of 2,4-bis(5-tetrazolyl)pyridine, 1 ml of triethylamine and 1.63 g of chloromethylphthalimide in 4.6 ml of abs. DMF was stirred at room temperature for 48 h and then evaporated, and the residue was purified on a silica gel column (200 g) with ethyl acetate/heptane 1:1 as eluent: 100 mg of 8, colorless crystals of melting point 224°–226° C. (decomposition).

$^1H$ NMR (60 MHz, $CDCl_3$) δ=5.6 (s, 4H), 7.0 (s, 4H), 7.7–8.2 (sh, 8H), 8.3 (dd, J=5 Hz, J'=2 Hz), 9.0 (d, J=6 Hz, 1H), 9.1 (s, 1H) ppm. $C_{25}H_{16}N_{11}O_4$ calc. 534 found 534 ($M^+$+$H^+$)

2,4-bis[2-(Succinimidomethyl)-5-tetrazolyl]pyridine (9)

A solution of 0.94 g of 2,4-bis(5-tetrazolyl)pyridine, 1.7 ml of triethylamine and 1.3 g of N-chloromethylsuccinimide in 10 ml of abs. DMF was stirred at room temperature for 24 h. The mixture was then partitioned between ethyl acetate and $H_2O$, and the organic phases were dried and evaporated. The residue was 2.05 g of an oil, which was purified on a silica gel column (40 g) with ethyl acetate as eluent. 0.72 g of 9 was obtained, colorless crystals of melting point 190°–192° C.

$^1H$ NMR (60 MHz, DMSO-$d_6$) δ=2.6 (s, 4H), 2.7 (s, 4H), 6.3 (s, 2H), 6.6 (s, 2H), 8.2 (dd, J=5 Hz, J'=2 Hz, 1H), 8.7 (s, 1H), 9.1 (d, J=6 Hz, 1H) ppm. $C_{17}H_{16}N_{11}O_4$ calc. 438 found 438 ($M^+$+$H^+$)

2,4-bis [2-(N,N-Dimethylcarbamoyl)-5-tetrazolyl]pyridine (10)

A solution of 0.5 g of 2,4-bis(5-tetrazolyl)pyridine, 1.6 ml of triethylamine and 0.43 ml of dimethylcarbamoyl chloride in 5 ml of abs. DMF was stirred at room temperature for 24 h, excess dimethylcarbamoyl chloride was decomposed with methanol, and the mixture was then concentrated in vacuo. The result was 1.86 g of an oil which was purified on a silica gel column (40 g) with $CH_2Cl_2$ methanol, gradient 20:1 to 9:1, as eluent. 0.38 g of 10 was obtained, colorless crystals of melting point 150° C. (decomposition).

$^1$H NMR (60 MHz, CDCl$_3$) δ=3.2 (s, 6H), 3.3 (s, 6H), 8.3 (dd, J=5 Hz, J'=2 Hz, 1H), 9.0–9.2 (sh, 2H) ppm. C$_{13}$H$_{16}$N$_{11}$O$_2$ calc. 358 found 358 (M$^+$+H$^+$)

2,4-bis[2-(4-Methyl-1,3-dioxol-2-on-5-ylmethyl )-5-tetrazolyl]pyridine (11)

A solution of 1.0 g of 2,4-bis(5-tetrazolyl)pyridine, 1.8 ml of triethylamine and 1.83 g of 5-bromomethyl-4-methyl-1,3-dioxol-2-one in 10 ml of abs. DMF was stirred at room temperature for 5 h and then evaporated in vacuo. The residue was purified on a silica gel column (160 g) with n-heptane/ethyl.acetate, gradient 1:1 to 1:3, as eluent. 0.24 g of 11 was obtained, colorless crystals, melting point 150°–152° C. (pentane/CH$_2$Cl$_2$).

$^1$H NMR (60 MHz, CDCl$_3$) δ=2.2 (s, 3H), 2.3 (s, 3H), 5.7 (s, 2H), 6.15 (s, 2H), 8.3 (d, J=5 Hz, 1H), 8.9 (d, J=6 Hz, 1H), 9.2 (s, 1H) ppm. C$_{17}$H$_{13}$N$_9$O$_6$ calc. 440 found 440 (M$^+$+H$^+$)

Isomeric 2,4-bis(ethoxycarbonylmethyl-5-tetrazolyl)pyridines (12a, b)

A solution of 1.5 g of bis(5-tetrazolyl)pyridine, 2.7 ml of triethylamine and 1.65 ml of ethyl iodoacetate in 10 ml of DMF was stirred at 60° C. for 3 h. After the reaction had been checked by TLC, a further 0.5 ml of ethyl iodoacetate was added. After a further 3 h at 60° C., the mixture was cooled to room temperature, diluted with ether and filtered, and the filtrate was evaporated in vacuo. The residue was purified by chromatography on a silica gel column (200 g) with ethyl acetate as eluent. 1.11 g of 12a were obtained, colorless crystals of melting point 85°–87° C.

$^1$H NMR (60 MHz, CDCl$_3$) δ=1.2 (t, J=8 Hz, 3H), 1.4 (t, J=8 Hz, 3H), 4.3 (q, J=8 Hz, 2H), 4.3 (q, J=8 Hz, 2H), 5.5 (s, 2H), 5.75 (s, 2H), 8.2 (dd, J=6 Hz, J'=2 Hz, 1H), 8.7 (d, J=5 Hz, 1H), 9.2 (s, 1H) ppm. C$_{15}$H$_{18}$N$_9$O$_4$ calc. 388 found 388 (M$^+$+H$^+$)

and 0.87 g of 12b, colorless crystals of melting point 143°–144° C., $^1$H NMR (60 MHz, CDCl$_3$) δ=1.3 (t, J=8 Hz, 3H), 1.35 (t, J=8 Hz, 3H), 4.25 (q, J=8 Hz, 2H), 4.3 (q, J=8 Hz, 2H), 5.5 (s, 4H), 8.2 (dd, J=6 Hz, J'=2 Hz, 1H), 9.0 (sh, 2H) ppm. C$_{15}$H$_{18}$N$_9$O$_4$ calc. 388 found 388 (M$^+$+H$^+$)

2,4-bis[2-(2-Morpholinoethyl)-5-tetrazolyl]pyridine (13)

A solution of 0.5 g of 2,4-bis(5-tetrazolyl)pyridine, 1.2 ml of triethylamine and 0.8 g of N-(2-chloroacetyl)-morpholine hydrochloride in 5 ml of abs. DMF was stirred at room temperature for 5 days, then diluted with ether and filtered, and the filtrate was evaporated in vacuo. The residue was purified by chromatography on a silica gel column (100 g) with CH$_2$Cl$_2$/methanol 40:1 as eluent. 214 g of 13 were obtained as a colorless viscous oil.

$^1$H NMR (60 MHz, CDCl$_3$) δ=2.1 (t, J=5 Hz, 4H), 2.2 (t, J=5 Hz, 4H), 2.9 (t, J=6 Hz, 2H), 3.1 (t, J=6 Hz, 2H), 3.5, (t, J=5 Hz, 4H), 3.7 (t, J=5 Hz, 4H), 4.9 (t, J=6 Hz, 2H), 5.2 (J=5 Hz, 2H), 8.2 (dd, J=6 Hz, J'=2 Hz, 1H), 8.9 (d, J=6 Hz, 1H), 9.1 (s, 1H) ppm. C$_{19}$H$_{28}$N$_{11}$O$_2$ calc. 442 found 442 (M$^+$+H$^+$)

2,4-bis(2-Benzyloxymethyl-5-tetrazolyl)pyridine (14)

2.8 ml of benzyl chloromethyl ether were added dropwise by syringe to a solution of 1.5 g of 2,4-bis(5-tetrazolyl)pyridine and 1.4 ml of triethylamine in 7 ml of abs. DMF, and the mixture was stirred at room temperature for 2 h. Subsequently, ethanol was added, the mixture was filtered and the filtrate was evaporated in vacuo. The residue was purified on a silica gel column (200 g) with ethyl acetate/hexane 1:1 as eluent. 0.56 g of 14 was obtained as a colorless viscous oil. A very pure product was obtained by subsequent chromatography on RP$_{18}$ silica gel with H$_2$O acetonitrile 1:3 as eluent.

$^1$H NMR (60 MHz, CDCl$_3$) δ=4.8 (s, 4H), 6.1 (2s, 4H), 7.4 (2s, 12H), 8.2 (dd, J=6 Hz, J'=2 Hz, 1H), 9.0 (sh, 2H) ppm. C$_{23}$H$_{22}$N$_9$O$_2$ calc. 456 found 456 (M$^+$+H$^+$)

Isomeric 2,5-bis(benzyloxymethyl-5-tetrazolyl)pyridines (15 a–d)

In analogy to the above procedure, 1.5 g of 2,5-bis(5-tetrazolyl)pyridine were reacted with 2.8 ml of benzyl chloromethyl ether. Chromatography of the crude product on silica gel (200 g) with heptane/ethyl acetate 1:1 as eluent provided all the isomeric substitution products. The following were obtained in the sequence of elution:

15a, colorless needles, melting point 103°–104° C. (heptane/ethyl acetate)

$^1$H NMR (CDCl$_3$, 60 MHz) δ=4.75 (s, 2H), 4.80 (s, 2H), 6.1 (s, 2H), 6.5 (s, 2H), 7.35 (s, 5H), 7.40 (s, 5H), 8.7 (sh, 2H), 9.6 (bs, 1H) ppm C$_{23}$H$_{22}$N$_9$O$_2$ calc. 456 found 456 (M$^+$+H$^+$)

15b, colorless crystalline powder, melting point 137.5°–138.5° C. (heptane/ethyl acetate), $^1$H NMR (CDCl$_3$, 60 MHz) δ=4.75 (s, 4H), 6.05 and 6.10 (s, each 2H), 7.5 (s, 10H), 8.6 (m, 2H), 9.65 (bs, 1H) ppm C$_{23}$H$_{22}$N$_9$O$_2$ calc. 456 found 456 (M$^+$+H$^+$)

15c, colorless fine needles, melting point 132°–133° C. (acetate/ethyl heptane), $^1$H NMR (CDCl$_3$, 60 MHz) δ=4.7 (s, 2H), 4.8 (s, 2H), 5.9 (s, 2H), 6.5 (s, 2H), 7.3 (s, 5H), 7.4 (s, 5H), 8.6 (d, J=Hz, 2H), 9.4 (s, 1H) ppm C$_{23}$H$_{22}$N$_9$O$_2$ calc. 456 found 456 (M$^+$+H$^+$)

15d, colorless soft needles, melting point 120.5°–121° C. (heptane/ethyl acetate), $^1$H NMR (CDCl$_3$, 60 MHz ) δ=4.7 (s, 4H), 5.9 (s, 2H), 6.1 (s, 2H), 7.4 (s, 10H), 8.55 (s, 2H), 9.5 (bs, 1H) ppm. C$_{23}$H$_{22}$N$_9$O$_2$ calc. 456 found 456 (M$^+$+ H$^+$)

We claim:

1. A method for inhibiting proline hydroxylase and lysine hydroxylase by administration to a host of an effective amount of a compound of formula I

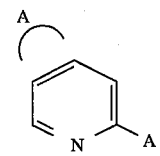

where A is

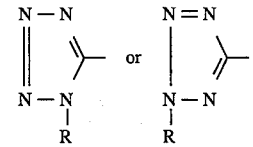

and where R is H or an unsubstituted (C$_1$–C$_6$)alkyl or a physiologically tolerated salt of said compound of formula I.

* * * * *